United States Patent
Tohda et al.

(10) Patent No.: US 6,235,499 B1
(45) Date of Patent: May 22, 2001

(54) **METHOD FOR TRANSFORMING *SCHIZOSACCHAROMYCES POMBE***

(75) Inventors: Hideki Tohda; Yuko Hama, both of Yokohama (JP)

(73) Assignee: Asahi Glass Company, Limited, Tokyo (JP)

(*) Notice: Subject to any disclaimer, the term of this patent is extended or adjusted under 35 U.S.C. 154(b) by 0 days.

(21) Appl. No.: 09/515,326

(22) Filed: Feb. 29, 2000

(30) Foreign Application Priority Data

Mar. 18, 1999 (JP) .................................................. 11-074342

(51) Int. Cl.$^7$ ............................ C12P 21/06; C07H 21/04; C12N 15/74; C12N 1/16
(52) U.S. Cl. ..................... 435/69.1; 435/254.2; 435/477; 536/23.1
(58) Field of Search ............................... 435/69.1, 254.2; 536/23.1

(56) References Cited

U.S. PATENT DOCUMENTS

| | | | |
|---|---|---|---|
| 5,817,478 | 10/1998 | Tohda et al. | 435/69.1 |
| 5,919,654 | 7/1999 | Hama et al. | 435/69.1 |

*Primary Examiner*—Robert A. Schwartzman
*Assistant Examiner*—Katherine F Davis
(74) *Attorney, Agent, or Firm*—Oblon, Spivak, McClelland, Maier & Neustadt, P.C.

(57) ABSTRACT

A method for transforming *Schizosaccharomyces pombe* which comprises integrating a vector into a chromosome of *Schizosaccharomyces pombe* through homologous recombination, wherein the vector has an expression cassette containing a heterologous protein structural gene and a promoter and a gene segment which induces homologous recombination of the chromosome and has lost a replication origin which functions in cells of an organism other than *Schizosaccharomyces pombe* required for construction of the vector.

16 Claims, No Drawings

METHOD FOR TRANSFORMING *SCHIZOSACCHAROMYCES POMBE*

BACKGROUND OF THE INVENTION

1. Field of the Invention

The present invention relates to a method for transforming the fission yeast *Schizosaccharomyces pombe*, particularly a method for transfer of a heterologous protein structural gene to its chromosome through homologous recombination. The present invention also relates to a vector for use in the transformation method, a *Schizosaccharomyces pombe* transformant obtained by the method and a method for producing a heterologous protein by using the *Schizosaccharomyces pombe* transformant.

2. Discussion of Background

The gene recombination technology is applied in various industries for production of heterologous proteins by usually using *Escherichia coli*, the budding yeast *Saccharomyces cerevisiae*, the methanol-assimilative yeast *Pichia pastoris*, insect cells and animal cells as the hosts. Ideally, any natural and artificial proteins could be produced, and in recent years, attempts have been made to produce not only purified proteins but also various chemical substances.

However, no "general host" that enables efficient production of any protein or chemical substance has been developed yet, and individual production systems have been developed for different target proteins and chemical substances by trial and error. Therefore, a further technical breakthrough is demanded in each expression system.

For production of heterologous proteins, especially eucaryotic proteins, use of eucaryotic microorganisms is considered as the best approach. Yeasts are very popular due to its long intimate relation with human life as a foodstuff in human history, have established large scale culture methods and have no endogenous substances detrimental to the human body unlike other expression systems. Various expression systems using yeasts as hosts have been developed so far (Yeast, 8, 423 (1992)).

In particular, a fission yeast, *Schizosaccharomyces pombe* (hereinafter referred to as *S. pombe*) is said to be closer to animal cells than other yeasts inclusive of a budding yeast *Saccharomyces cerevisiae* in various properties such as cell cycle, chromosomal structure and RNA splicing, and the post-translational modification such as acetylation, phosphorylation and glycosilation of proteins produced in *S. pombe* seems similar to that in animal cells (Cell, 45, 781 (1986); Nature, 318, 78 (1985); J. Cell. Boil., 109, 2693 (1989)).

Besides, despite being a eucaryote, *S. pombe* has been studied extensively for its high versatility in genetics, molecular biology and cell biology as a unicellular organism (Molecular biology of the fission yeast, Academic Press (1989)). Technological studies have been already done for DNA recombination in *S. pombe* (Experiments with Fission Yeast, Cold Spring Harbor Laboratory press (1993)).

For these reasons, *Schizosaccharomyces pombe* is considered advantageous as the host for expression of inherent proteins in animal cells. Use of *Schizosaccharomyces pombe* is expected to provide a gene product closer to its natural form in animal cells. However, *Schizosaccharomyces pombe* is far behind the budding yeast in studies on gene expression, and the literature on gene expression using *Schizosaccharomyces pombe* has been scant (JP-A-61-181397, JP-A-2-283288, JP-A-4-63596). This is because development of expression vectors which have powerful promoters, are stable in *S. pombe* cells and are suitable and convenient for introduction of a gene has been retarded.

Recent development of high-expressivity vectors for the fission yeast such as an inducible expression vector using the promoter region for the nmt1$^+$ gene (pREP1) and vectors having an animal virus-derived promoter region eventually opened the way to large scale production of heterologous proteins in *S. pombe* (JP-A-5-15380, JP-A-7-163373, WO96/23890, JP-A-10-234375).

These technologies have facilitated production of many intracellular proteins and provided useful expression systems. In fact, *Schizosaccharomyces pombe* has gradually come into wide use as a host for expression of heterologous protein genes and is known to be suited especially to expression of genes from animal cells including human cells (Foreign gene expression in fission yeast *Schizosaccharomyces pombe*, R. G. Landes (1997)). For its advanced membrane structures including the Goldi body and the endoplasmic reticulum, *Schizosaccharomyces pombe* is also used for expression of membrane proteins and shows high level expression.

A conventional *S. pombe* transformant carries the expression vector introduced therein as an extrachromosomal genetic material (a plasmid). However, the extrachromosomal genetic material sometimes slips out and disappears from *S. pombe* cells during incubation. Therefore, in order to stably maintain a vector having a heterologous protein structural gene in cells, it is preferable to integrate the vector into a chromosome of *S. pombe*. Chromosomal integration of vectors usually involves homologous recombination. A vector capable of being integrated into a chromosome through homologous recombination will be referred to as an integrative vector hereinafter.

Integration of integrative vectors into chromosomes of *S. pombe* has been reported already (J. Ind. Microbiol., 4, 409 (1989); Appl. Microbiol. Biotechnol., 49, 45 (1998)). However, conventional integrative vectors can not provide *S. pombe* transformants which show satisfactory expression of heterologous proteins.

The present inventors investigated the reasons and have found that one of the reasons is the low efficiency in chromosomal integration of integrative vectors into *S. pombe* attributable to many unintegrated vector molecules present as plasmids in *S. pombe* cells. On the other hand, it is generally known that more than one copy of an integrative vector can be integrated at one site in a chromosomal gene, and the expression of a heterologous protein is expected to increase with the number of copies of an integrative vector integrated at one gene site. The present inventors found that conventionally obtainable *S. pombe* transformants have a few copies of an integrative vector at one site in a chromosome and speculated that this might be the reason of the unsatisfactory expression of heterologous proteins. The present inventors have conducted extensive research into the reasons of the above-mentioned low efficiency in chromosomal integration of integrative vectors into *S. pombe* and the insufficient number of copies of an integrative vector integrated at one gene site, and as a result, have found that the "replication origin in an integral vector which functions in cells other than *S. pombe* cells required for construction of the vector" is responsible for them.

Construction of a vector such as an integrative vector essentially involves replication of the vector by using cells which are easy to genetically engineer. *Escherichia coli* is a typical example of such cells and frequently used for construction of vectors. The presence of the replication origin from *Escherichia coli* called "ori" in a vector permits replication of the vector in *Escherichia coli*. The present inventors have found that the presence of the replication origin lowers the efficiency in chromosomal integration of integrative vectors into *S. pombe* and decrease the number of integrated copies.

On the basis of the above-mentioned discoveries, the present inventors have found that the above-mentioned problem is solved by chromosomal integration of an integrative vector into *S. pombe* after removal of the above-mentioned replication origin, namely that an integrative vector which has lost the above-mentioned replication origin is integrated with improved efficiency and increases the number of copies integrated at one site of a chromosomal gene.

The present invention provides the following transformation methods, vector, transformant and method for protein production using the transformant:

a method for transforming *Schizosaccharomyces pombe* which comprises integrating a vector into a chromosome of *Schizosaccharomyces pombe* through homologous recombination, wherein the vector has an expression cassette containing a heterologous protein structural gene and a promoter and a gene segment which induces homologous recombination of the chromosome and has lost a replication origin which functions in cells of an organism other than *Schizosaccharomyces pombe* required for construction of the vector;

a method for transforming *Schizosaccharomyces pombe* which comprises constructing a homologous recombination vector having an expression cassette containing a heterologous protein structural gene and a promoter, a gene segment which induces homologous recombination of a chromosome of *Schizosaccharomyces pombe* and a replication origin from *Escherichia coli* by using *Escherichia coli*, removing the replication origin from *Escherichia coli* and integrating the vector into the chromosome of *Schizosaccharomyces pombe*;

a vector for introduction of a heterologous protein structural gene into a chromosome of *Schizosaccharomyces pombe* by homologous recombination, which has an expression cassette containing a heterologous protein structural gene and a promoter and a gene segment which induces homologous recombination of the chromosome and has lost a replication origin which functions in cells of an organism other than *Schizosaccharomyces pombe* required for construction of the vector;

a *Schizosaccharomyces pombe* transformant obtained by either of the above-mentioned methods; and a method for producing a heterologous protein which comprises incubating the above-mentioned *Schizosaccharomyces pombe* transformant and recovering the produced heterologous protein.

The expression cassette in the present invention is a DNA set necessary for expression of the heterologous protein encoded by a heterologous protein structural gene integrated into a chromosome of *S. pombe*. The expression cassette contains a heterologous protein structural gene and a promoter which promotes the expression of the structural gene and usually further contains at least one of a terminator, a 5'-untranslated region and a 3'-untranslated region, preferably a heterologous protein structural gene, a promoter, a terminator, a 5'-untranslated region and 3'-untranslated region altogether. It may contain a secretion signal gene linked to the heterologous protein structural gene.

The "heterologous protein" means a protein which *S. pombe* does not inherently produce (which is not encoded by any gene in *S. pombe*), preferably a protein produced by the human or any other mammal in view of industrial values. The ultimate object of the present invention is production of the heterologous protein.

The "gene segment which induces homologous recombination of a chromosome of *Schizosaccharomyces pombe*" is a gene homologous to a gene in a *S. pombe* chromosome. Homologous recombination occurs when a *S. pombe* chromosomal gene and a homologous gene segment in the vector is genetically exchanged upon synapsis. The chromosome of *S. pombe* must contain at least one copy of the *S. pombe* chromosomal gene as the target of the gene segment in the vector and may contain plural copies of the gene. Though more vector molecules are integrated as the number of copies of the target gene increases, satisfactorily many vector molecules can be integrated with high efficiency even into a *S. pombe* chromosome which contain only one copy of the target.

As the target gene, a gene which serves as a auxotrophic marker in *S. pombe* is preferable. As such a gene, preferable is an isopropylmalate dehydrogenase gene, an orotidine phosphate decarboxylase gene, a histidinol-phosphate aminotransferase gene or a phosphoribosyl-AMP cyclohydrolase gene in *S. pombe*. It is preferred that such a gene in the *S. pombe* chromosome which integrates the vector serves as an auxotrophic marker, namely is functionally deficient, while the gene segment in the vector homologous to such a gene can restore the auxotrophy of *S. pombe* (restore its function).

In particular, the gene segment in the vector is the wild type of an isopropylmalate dehydrogenase gene (leu1$^+$), an orotidine phosphate decarboxylase gene (ura4$^+$), a histidinol-phosphate aminotransferase gene (his3$^+$) or a phosphoribosyl-AMP cyclohydrolase gene (his7$^+$) in *S. pombe*. The gene segment in the vector in (or according to) the present invention is hereinafter referred to as "the homologous gene segment".

"The replication origin which functions in cells of an organism other than *S. pombe* required for construction of the vector" means such a replication origin as described above. Namely, the cells of an organism other than *S. pombe* means cells which are easy to genetically engineer such as *E. coli* cells, and the replication origin means a replication origin essential for construction of an integrative vector in the cells. Admittedly, *E. coli* cells are exclusively used in practical genetic engineering for construction of vectors, and the replication origin called "ori" is exclusively used as the replication origin which is introduced into vectors for replication of the vectors. Hereinafter, the present invention will be explained by taking the *E. coli* replication origin as an example. The replication origin is also referred to simply as "the replication origin" hereinafter.

The vector in (or of) the present invention which has the above-mentioned expression cassette and homologous gene segment and has lost the replication origin is referred to as "the integrative vector of the present invention" hereinafter. The integrative vector of the present invention is obtainable by removing the replication origin from a vector having the above-mentioned expression cassette, homologous gene segment and replication origin, which will be referred to as "the precursor vector" hereinafter. The precursor vector can be constructed by methods similar to those employed for construction of expression vectors of the non-integrative type (to be extrachromosomally introduced into *S. pombe*). Even from an expression vector which lacks the homologous gene segment, the precursor vector can be constructed if the homologous gene segment is introduced when the expression vector is constructed.

The expression vector used for construction of the precursor vector is preferably a vector used for transformation of S. pombe and is preferably constructed by the same method, though there is no particular restriction on the vector or the method for its construction. In particular, it is preferred to apply the expression vectors disclosed in JP-A-5-15380, JP-A-7-163373, WO96/23890 and JP-A-10-234375 mentioned above and methods for their construction for construction of the precursor vector. The integrative vector of the present invention is obtainable by constructing the precursor vector and removing the replication origin by common techniques in genetic engineering.

In the present invention, the integrative vector of the present invention is in the form of a circular or linear DNA. The integrative vector has to be introduced into cells in the form of a linear DNA before integrated into a chromosome, though the integrative vector constructed by the above-mentioned method is usually in the form of a circular DNA. Therefore, the integrative vector of the present invention obtained in a circular form is usually cut open to a linear form before introduced into S. pombe cells. For this purpose, it is necessary to make a cut within the homologous gene segment to open the circular structure of the integrative vector of the present invention. Namely, the integrative vector of the present invention opened up into a linear form has to have part of the homologous gene segment at one end and the rest of the homologous gene segment at the other end. The integrative vector of the present invention can be constructed in a linear form so as to have such a structure without cutting open a circular structure of the integrative vector of the present invention.

The present inventors have found a simple method for obtaining the integrative vector of the present invention in a linear form having the above-mentioned structure. It is common to remove the replication origin from the circular precursor vector and then cut open the resulting circular integrative vector of the present invention. However, it is cumbersome to remove the replication origin from the circular precursor vector to make the integrative vector of the present invention in a circular form.

The present inventors have found a one step method for producing the integrative vector of the present invention in a linear form by removing the replication origin from the precursor vector, which comprises constructing the precursor vector in a circular form having the replication origin at a site where the homologous gene segment is to be cut (namely between the two ends of the integrative vector of the present invention in a linear form) and then removing the replication origin from the circular precursor vector to give the integrative vector of the present invention in a linear form. Because the homologous gene segment usually does not has to function during the construction of the precursor vector, the precursor vector having such a structure can be easily constructed.

The integrative vector of the present invention may have genes other than replication origins, for example, genes used for construction of the vector, in addition to the above-mentioned expression cassette and homologous gene segment. Such genes may be, for example, antibiotic resistance genes (such as neomycin resistance genes) which serve as markers for selection of the vector. Otherwise, such genes used for construction of the vector may be removed before integration of the vector into a chromosome like the replication origin.

The promoter in the expression cassette is not particularly limited, but is preferably a promoter which actively promotes the expression of the heterologous protein structural gene, such as promoters from animal viruses disclosed in JP-A-5-15380, JP-A-7-163373, WO96/23890 and JP-A-10-234375 mentioned above. Particularly preferred are CMV promoter and SV40 promoter. There may be a secretion signal gene functional in S. pombe upstream from the heterologous protein structural gene. As such a secretion signal gene, the secretion signal gene disclosed in WO96/23890 mentioned above is preferable.

In the present invention, the integrative vector of the present invention may have more than one copy of the expression cassette. Even if the integrative vector can not be integrated at more than one site in a S. pombe chromosome, more than one molecules of the integrative vector can be integrated there. In such a case, even if the integrative vector has only one copy of the expression cassette, plural copies of the expression cassette are integrated into the chromosome. If the integrative vector has more than one copy of the expression cassette, much more copies of the expression cassette are integrated. Further, if the integrative vector is integrated at more than one site in a S. pombe chromosome, further more copies of the expression cassette are integrated. The heterologous protein is expressed more efficiently as the number of copies of the expression cassette integrated in a chromosome increases.

The number of copies of the expression cassette in the integrative vector is not particularly limited, but it is preferably at most 20, particularly at most 10, because the presence of too many copies of the expression cassette likely to render the integrative vector too large to be integrated efficiently. The total number of copies of the expression cassette integrated in the S. pombe chromosomes is not limited either, but it is preferably at most 50, particularly at most 30, because the presence of too many copies of the expression cassette is likely to lower the expression efficiency.

As the gene in the homologous gene segment, a gene homologous to the wild-type isopropylmalate dehydrogenase (leu1$^+$) gene in S. pombe is particularly preferable. Though the isopropylmalate dehydrogenase gene is present at only one site in the chromosomes of S. pombe, the integrative vector can provide a S. pombe transformant which efficiently expresses the heterologous protein because plural copies of the integrative vector can be integrated there. As the S. pombe strain to be transformed, a S. pombe strain having an auxotrophic marker, which facilitates selection of transformants, is preferable. For example, introduction of an integrative vector having the above-mentioned wild-type isopropylmalate dehydrogenase (leu1$^+$) gene cancels the leucine auxotrophy of a S. pombe strain (such as a leu1-32 mutant strain) which has lost the function of the isopropylmalate dehydrogenase gene. Thus, such a auxotrophic change can be utilized for selection of transformants.

The Examples of the present invention which will be described later are outlined below.

Firstly, the well-known leu1$^+$ gene was obtained and integrated into a conventional expression vector (having the above-mentioned replication origin "ori"). The resulting integrative vector was used to transform a leu1-32 mutant strain of S. pombe (a leucine auxotroph), and a transformant carrying the expression cassette containing the desired heterologous protein structural gene was selected through screening for cancellation of the leucine auxotrophy. The transformant was stable, but the production level of the desired heterologous protein was low. On the other hand, many clones having the introduced integrative vector as a plasmid were obtained, and it was relatively difficult to obtain clones having plural copies of the expression cassette in a chromosome

EXAMPLES 1 AND 2

Then, an integrative vector without the replication origin from E. coli was constructed. Namely, the linear integrative vector was prepared by constructing an integrative vector having the replication origin shifted to the SplI site in the leu1$^+$ gene and then cutting off the replication origin. The vector was used to transform the lue1-32 mutant strain of S. pombe and transformants carrying the expression cassette containing the desired heterologous protein structural gene were selected through screening for cancellation of the leucine auxotrophy. Thus, transformants which produce the desired heterologous protein at a level as high as or higher than the transformants obtained with the extrachromosomal expression vector were obtained

EXAMPLES 3 TO 6

Now, the present invention will be described with reference to specific Examples. However, the present invention is no by means restricted to those specific Examples. Examples 1 and 2 are reference examples, and Examples 3 to 6 are working examples. For amplification of the vectors constructed in those Examples, an E. coli DH5 strain (Toyobo Co., Ltd) was used (which is specifically described in Example 3, but omitted in the other Examples).

EXAMPLE 1

Construction of a Plasmid-based Production System

PCR using a vector pEGFP-1 containing an Aequorea victria green fluorescent protein variant (hereinafter referred to as EGFP) gene purchased from Clonetech as the template was performed to amplify the 720 bp-region from the initiation codon to the termination codon. After terminal trimming utilizing the NcoI-tag attached to the 5'-primer and HindIII tag attached to the 3'-primer, the resulting segment was inserted between AflIII-HindIII in a multicloning vector pTL2M5 (4657 bp; obtained by removing the poly dA and the SV40 terminator region behind the 3'-UTR from a multicloning vector pTL2M as disclosed in JP-A-7-163373) to give a recombinant vector pTL2EGFP.

A S. pombe transformant ASP170 was obtained by using pTL2EGFP thus obtained in accordance with JP-A-7-163373 and tested for EGFP production in YPD100 medium (a liquid medium containing 1 wt % Bacto-yeast extract (Difco), 2 wt % Bacto-Peptone (Difco), 2 wt % glucose (Wako Pure Chemical Industries, Ltd.) and 100 μg/L Geneticin (Life Technology).

The results indicate that the production was 143 CU (Corona unit; the fluorescence at 630 nm measured by a microplate reader MTP-32 (Corona Electrics) with excitation light of 590 nm) of 100 μL culture and the production efficiency was 286 CU/g (converted from the fluorescence of 1 mL culture in terms of the dry cell weight). After 50 generations of passage, the production and production efficiency remained unchanged in YPD100 medium but as low as 26 CU and 53.2 CU/g, respectively, in YPD medium (a liquid medium containing 1 wt % Bacto-yeast extract (Difco), 2 wt % Bacto-Peptone (Difco) and 2 wt % glucose (Wako Pure Chemical Industries, Ltd.).

EXAMPLE 2

Conventional Construction of an Integrative Production System

A conventional plasmid, pYK320 (Curr. Genet., 14, 375 (1988)) was digested with a restriction enzyme AccI (Toyobo Co., Ltd), and the leu1$^+$ segment of about 3.5 kbp obtained in gel was purified by the glass powder method (EASY TRAP, Takara Shuzo Co., Ltd.). The segment was joined with the segment (about 5.0 kbp) obtained by digestion of a recombinant vector pTL2EGFP with a restriction enzyme Bst11071 (Takara Shuzo Co., Ltd.) by ligation using a ligation kit (Takara Shuzo Co., Ltd.). The ligation product was used to transform the E. coli DH5 strain to give the desired recombinant vector pTL2EGFP-LR (9047 bp). 1 μg of the recombinant vector pTL2EGFP-LR was digested with a restriction enzyme SplI (Takara Shuzo Co., Ltd.) and used to obtain S. pombe transformants ASP218 and ASP219 in accordance with JP-A-7-163373, and the transformants were tested for EGFP production in YPD medium.

The results indicate a production of 11 CU and a production efficiency of 24.3 CU/g. The production and production efficiency remained unchanged after 50 generations of passage. Preparation of more productive clones was attempted, but strains with higher productivity that are stable even after 50 generations of passage were not obtained because strains carrying the vector as a plasmid predominated (as verified by genome analysis pulse field gel electrophoresis).

EXAMPLE 3

Construction of an Integrative Production System pTL2EGFP-LP constructed in Example 2 was digested with a restriction enzyme SplI, and a PCR amplification product of pBR322 (Toyobo Co., Ltd.) having the replication origin and the ampicillin resistance gene from E. coli with a SplI tag at each end was inserted and introduced into E. coli DH5 strain to give a recombinant vector pTL2EGFP-LR(OAIF) (11.7 kbp). The pTL2EGFP-LR(OAIF) fragment obtained by restriction digestion with AccI (Takara Shuzo Co., Ltd.) followed by blunting (using DNA Blunting Kit, Takara Shuzo Co., Ltd.) and the pTL2EGFP-LP(OAIF) fragment obtained by partial restriction digestion with HpaI (Takara Shuzo Co., Ltd.) and complete restriction digestion with Bst1107I were joined and introduced into E. coli DH5 strain to give a recombinant vector pTL2EGFP-XLRF (9.1 kbp). A fragment of pTL2EGFP-XLRF obtained by double restriction digestion with SpeI (Takara Shuzo Co., Ltd.) and AccIII (Toyobo Co., Ltd) and a fragment of pTL2EGFP-LR obtained by double restriction digestion with SpeI and AccIII were joined and introduced into E. coli DH5 strain to give a recombinant vector pTL2EGFP-XL (9048 bp).

1 μg of the recombinant vector pTL2EGFP-XL was digested with a restriction enzyme SplI and used for transformation of S. pombe in accordance with JP-A-7-163373 to give 5 types of a S. pombe transformant ASP285. They were tested for EGFP production in YPD medium.

The results indicate that the productions and the production efficiencies were 12 CU and 28.0 CU/g, 25 CU and 51.8 CU/g, 40 CU and 78.1 CU/g, 59 CU and 115.7 CU/g and 81 CU and 167.9 CU/g in increasing order of production. These gradational productions and production efficiencies indicate integration of not only one copy but also plural copies. The productions and the production efficiencies remained unchanged even after 50 generations of passage, and genome analysis by pulse field gel electrophoresis ascertained the presence of plural copies of EGFP in the chromosomes.

EXAMPLE 4

Construction of a Duplicated Integrative Production System

A fragment of the recombinant vector pTL2EGFP-XL in Example 3 obtained by double restriction digestion with PvuI (Takara Shuzo Co., Ltd.) and SpeI followed by blunting and a fragment of pTL2EGFP-XL obtained by double restriction digestion with PvuI and AccI followed by blunting were joined to give a recombinant vector pTL2EGFP-2XL (10790 bp). 1 μg of the recombinant vector pTL2EGFP-2XL was digested with a restriction enzyme SpeI and used for transformation of S. pombe in accordance with JP-A-7-163373 to give a transformant ASP356. The transformant was tested for EGFP production in YPD medium.

The results indicate a production of 59 CU and a production efficiency of 118.2 CU/g. The production and production efficiency indicate integration of not only one copy but also plural copies of the duplicated expression cassette and remained unchanged even after 50 generations of passage.

EXAMPLE 5

Construction of a Quadruplicated Integrative Production System

A fragment of the recombinant vector pTL2EGFP-2XL in Example 4 obtained by double restriction digestion with PvuI and SpeI followed by blunting and a fragment of pTL2EGFP-2XL obtained by double restriction digestion with PvuI and AccI followed by blunting were joined to give a recombinant vector pTL2EGFP-4XL (14274 bp). 1 μg of the recombinant vector pTL2EGFP-4XL was digested with a restriction enzyme SpeI and used for transformation of S. pombe in accordance with JP-A-7-163373 to give a transformant ASP357. The transformant was tested for EGFP production in YPD medium.

The results indicate a production of 103 CU and a production efficiency of 192.5 CU/g. The production and production efficiency indicate integration of not only one copy but also plural copies of the quadruplicated expression cassette and remained unchanged even after 50 generations of passage.

EXAMPLE 6

Construction of an Octuplicated Integrative Production System

A fragment of the recombinant vector pTL2EGFP-4XL in Example 5 obtained by double restriction digestion with PvuI and SpeI followed by blunting and a fragment of pTL2EGFP-4XL obtained by double restriction digestion with PvuI and AccI followed by blunting were joined to give a recombinant vector pTL2EGFP-8XL (21242 bp). 1 μg of the recombinant vector pTL2EGFP-8XL was digested with a restriction enzyme SpeI and used in transformation of S. pombe in accordance with JP-A-7-163373 to give two types of a transformant ASP358. They were tested for EGFP production in YPD medium.

The results indicate that the productions and the production efficiencies were 99 CU and 202.5 CU/g, and 173 CU and 329.8 CU/g, respectively. These productions and production efficiencies indicate integration of not only one copy but also plural copies of the octuplicated expression cassette and are higher than those obtained with the plasmid-based (extrachromosomal type) production system in Example 1, and remained unchanged even after 50 generations of passage.

The integrative vector which lacks a replication origin from E. coli is efficiently integrated into a chromosome of S. pombe. The presence of plural copies of expression cassette in the integrative vector allows integration of more copies of the expression cassette. Therefore, it is possible to markedly improve the production of a heterologous protein and the efficiency of its production.

What is claimed is:

1. A method for transforming Schizosaccharomyces pombe which comprises integrating a vector into a chromosome of Schizosaccharomyces pombe through homologous recombination, wherein the vector has an expression cassette containing a heterologous protein structural gene and a promoter and a gene segment which induces homologous recombination of the chromosome and has lost a replication origin which functions in cells of an organism other than Schizosaccharomyces pombe required for construction of the vector, to provide transformed Schizosaccharomyces pombe.

2. The method according to claim 1, wherein the replication origin is a replication origin from Escherichia coli.

3. The method according to claim 1, wherein the replication origin was present in the gene segment which induces homologous recombination of the chromosome of Schizosaccharomyces pombe.

4. The method according to claim 1, wherein the gene segment which induces homologous recombination of the chromosome is homologous to an isopropylmalate dehydrogenase gene, an orotidine phosphate decarboxylase gene, a histidinol-phosphate aminotransferase gene or a phosphoribosyl-AMP cyclohydrolase gene in Schizosaccharomyces pombe.

5. The method according to claim 1, wherein the vector has at least two copies of the expression cassette.

6. A method for transforming Schizosaccharomyces pombe which comprises constructing a homologous recombination vector having an expression cassette containing a heterologous protein structural gene and a promoter, a gene segment which induces homologous recombination of a chromosome of Schizosaccharomyces pombe and a replication origin from Escherichia coli amplification in Escherichia coli, removing the replication origin from Escherichia coli and integrating the vector into the chromosome of Schizosaccharomyces pombe, to provide transformed Schizosaccharomyces pombe.

7. The method according to claim 6, wherein the replication origin is present in the gene segment which induces homologous recombination of the chromosome of Schizosaccharomyces pombe.

8. The method according to claim 6, wherein the gene segment which induces homologous recombination of the chromosome is homologous to an isopropylmalate dehydrogenase gene, an orotidine phosphate decarboxylase gene, a histidinol-phosphate aminotransferase gene or a phosphoribosyl-AMP cyclohydrolase gene in Schizosaccharomyces pombe.

9. The method according to claim 6, wherein the vector has at least two copies of the expression cassette.

10. A Schizosaccharomyces pombe transformant obtained by the method according to claim 1 or 6.

11. A method for producing a heterologous protein which comprises incubating the Schizosaccharomyces pombe transformant according to claim 10 and recovering the produced heterologous protein.

12. A vector for introduction of a heterologous protein structural gene into a chromosome of Schizosaccharomyces pombe by homologous recombination, which has an expression cassette containing a heterologous protein structural gene and a promoter and a gene segment which induces homologous recombination of the chromosome and has lost a replication origin which functions in cells of an organism other than *Schizosaccharomyces pombe* required for construction of the vector.

13. The vector according to claim 12, wherein the replication origin is a replication origin from *Escherichia coli.*

14. The vector according to claim 12, wherein the gene segment which induces homologous recombination of the chromosome is homologous to an isopropylmalate dehydrogenase gene, an orotidine phosphate decarboxylase gene, a histidinol-phosphate aminotransferase gene or a phosphoribosyl-AMP cyclohydrolase gene in *Schizosaccharomyces pombe.*

15. The vector according to claim 12, wherein the replication origin was present in the gene segment which induces homologous recombination of the chromosome of *Schizosaccharomyces pombe.*

16. The vector according to claim 12, which has at least two copies of the expression cassette.

* * * * *